US010792073B2

(12) United States Patent
Eisen

(10) Patent No.: US 10,792,073 B2
(45) Date of Patent: Oct. 6, 2020

(54) SKIN CARE APPARATUS

(71) Applicant: Lawrence D Eisen, Bethesda, MD (US)

(72) Inventor: Lawrence D Eisen, Bethesda, MD (US)

( * ) Notice: Subject to any disclaimer, the term of this patent is extended or adjusted under 35 U.S.C. 154(b) by 350 days.

(21) Appl. No.: 15/859,310

(22) Filed: Dec. 29, 2017

(65) Prior Publication Data

US 2019/0201054 A1    Jul. 4, 2019

(51) Int. Cl.
*A61B 17/30* (2006.01)
*A61B 17/54* (2006.01)
*A61B 17/00* (2006.01)

(52) U.S. Cl.
CPC .............. *A61B 17/54* (2013.01); *A61B 17/30* (2013.01); *A61B 2017/00539* (2013.01); *A61B 2017/00544* (2013.01); *A61B 2017/00747* (2013.01)

(58) Field of Classification Search
CPC ......... A61B 17/08; A61B 17/30; A61B 17/54; A61B 17/122; A61B 2017/00747; A61B 2017/00752; A61B 2017/00774; A61B 2017/301; A61B 2017/303; A61B 2017/305; A61B 17/50; A61B 2017/505; A61Q 19/00; A61M 5/425; A45D 26/0066; A47G 21/10; A47J 43/283; G04D 1/02; G04D 1/021; B25B 5/067; B25B 5/068; B25B 5/08; B25B 5/082; B25B 5/085; B25B 5/087; B25B 5/10; B25B 5/101; B25B 5/102; B25B 5/103; B25B 5/104; B25B 5/105; B25B 5/106; B25B 5/107; B25B 5/108; B25B 5/109; B25B 5/12; B25B 5/122; B25B 5/125; B25B 5/127; B25B 5/14; B25B 5/142; B25B 5/145; B25B 5/147; B25B 5/16; B25B 5/163; B25B 5/166; B25B 9/00; B25B 9/02; B25B 9/04; F16L 23/036; F16L 3/00; A61F 9/00736; A61F 9/00763
See application file for complete search history.

(56) References Cited

U.S. PATENT DOCUMENTS

| | | | | |
|---|---|---|---|---|
| 5,542,167 | A  * | 8/1996 | Nakamoto | ................ B25B 7/04 29/229 |
| 6,394,951 | B1 * | 5/2002 | Taylor | .............. A61B 17/00234 600/210 |
| 7,536,896 | B1 * | 5/2009 | Hung | ........................ B25B 7/04 29/751 |
| 2005/0070927 | A1 * | 3/2005 | Feinberg | .............. A61B 17/083 606/150 |

(Continued)

*Primary Examiner* — Darwin P Erezo
*Assistant Examiner* — Christian D Knauss

(57) ABSTRACT

A device includes a first arm having a first rotating member including a first gear coupled thereto and a first rotation imparting member fixed thereto, a second arm pivotally coupled to the first arm at proximal ends of the first arm and the second arm, the second arm having a second rotating member including a second gear coupled thereto and a second rotation imparting member fixed thereto, wherein when the first arm and the second arm are brought towards each other, the first rotation imparting member engages with the second gear to cause the second rotating member to rotate in a first direction, and the second rotation imparting member engages with the first gear to cause the first rotating member to rotate in a second direction, opposite the first direction.

20 Claims, 5 Drawing Sheets

(56) References Cited

U.S. PATENT DOCUMENTS

| | | | |
|---|---|---|---|
| 2008/0082111 A1* | 4/2008 | Jaffee | A61B 17/50 606/131 |
| 2010/0096871 A1* | 4/2010 | Ait-Mani | B25B 9/02 294/99.2 |
| 2013/0274743 A1* | 10/2013 | Banfalvi | A61B 17/29 606/51 |
| 2015/0257776 A1* | 9/2015 | Sauer | A61B 17/2804 606/207 |
| 2018/0040998 A1* | 2/2018 | Frenken | H01R 43/042 |

* cited by examiner

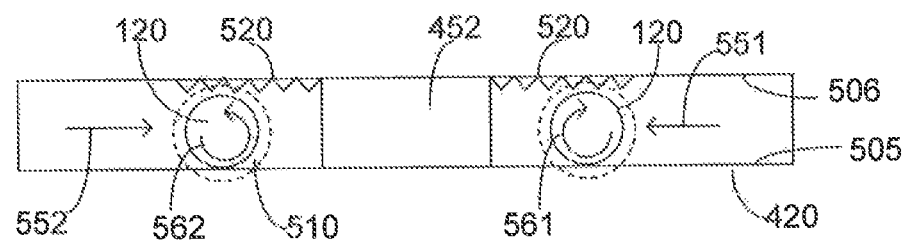
FIG. 5
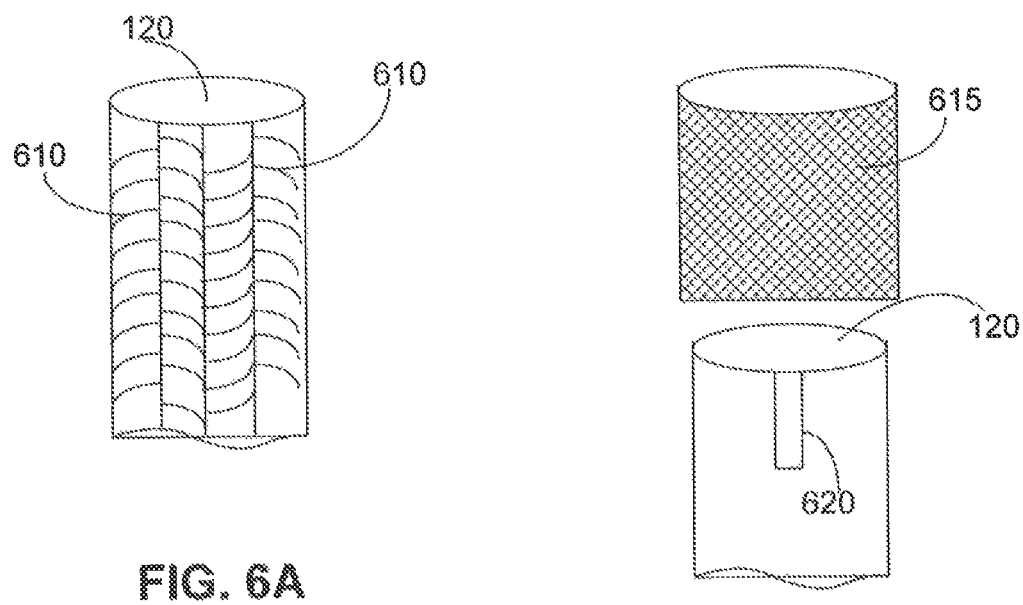
FIG. 6A
FIG. 6B

SKIN CARE APPARATUS

BACKGROUND

Acne is a skin condition characterized by facial blemishes. It is believed that this condition results from an obstruction of follicle openings on the skin or dermis that leads to the formation of a layer of keratinized cells commonly referred to as whiteheads and/or blackheads. Continued blockage of these follicle openings causes bacteria to form therein and, in turn, provokes an inflammatory response. It is thus sometimes desirable to remove the unwanted keratinized cells (i.e., blackheads, whiteheads) from follicle openings and thereafter keep the follicle openings clean in order to reduce recurrence of the condition.

Removing blackheads and whiteheads embedded in the dermis often requires the application of force to the affected area. Typically, two fingernail tips are pressed at complementary angles on opposite sides of the blemish to pinch the blackhead or whitehead outwards from the dermis. Although effective in exposing the underlying follicle opening, using one's fingernail tips to remove blemishes may inadvertently and undesirably cut surrounding areas of the dermis. In addition, when using one's fingernail tips to remove blemishes, bacteria and other germs residing under one's fingernails may come into contact with the freshly exposed follicle openings and/or any cuts on the dermis resulting from the pinching action of the fingernail tips.

SUMMARY

Embodiments of the present invention are directed to a skin care apparatus that, e.g., facilitates the treatment of skin blemishes, and that may also be used on other tissue. In accordance with one embodiment, a device includes a first arm having a first rotating member including a first gear coupled thereto and a first rotation imparting member fixed thereto, a second arm pivotally coupled to the first arm at proximal ends of the first arm and the second arm, the second arm having a second rotating member including a second gear coupled thereto and a second rotation imparting member fixed thereto, wherein when the first arm and the second arm are brought towards each other, the first rotation imparting member engages with the second gear to cause the second rotating member to rotate in a first direction, and the second rotation imparting member engages with the first gear to cause the first rotating member to rotate in a second direction, opposite the first direction, and thereby impart an outward pinching action when the rotating members are pressed against the dermis, e.g., at the base of a blemish.

In another embodiment, rotating members are arranged inside a housing with distal ends of the rotating members extending outside of the housing. Actuators are provided that not only cause the rotating members to approach each other by pressing on or squeezing the actuators, but also cause the rotating members to rotate counter to each other and thereby impart an outward pinching action when the rotating members are pressed against the dermis, e.g., at the base of a blemish.

BRIEF DESCRIPTION OF THE DRAWINGS

FIG. 5 shows a cross-sectional view through V-V in FIG. 4 of a channel that captures a pair of rotating members of the skin care apparatus in accordance with an example embodiment.

FIGS. 6A and 6B show the distal end of a rotating member, without and with an attachment, respectively, in accordance with an example embodiment.

DETAILED DESCRIPTION

Figure 1:
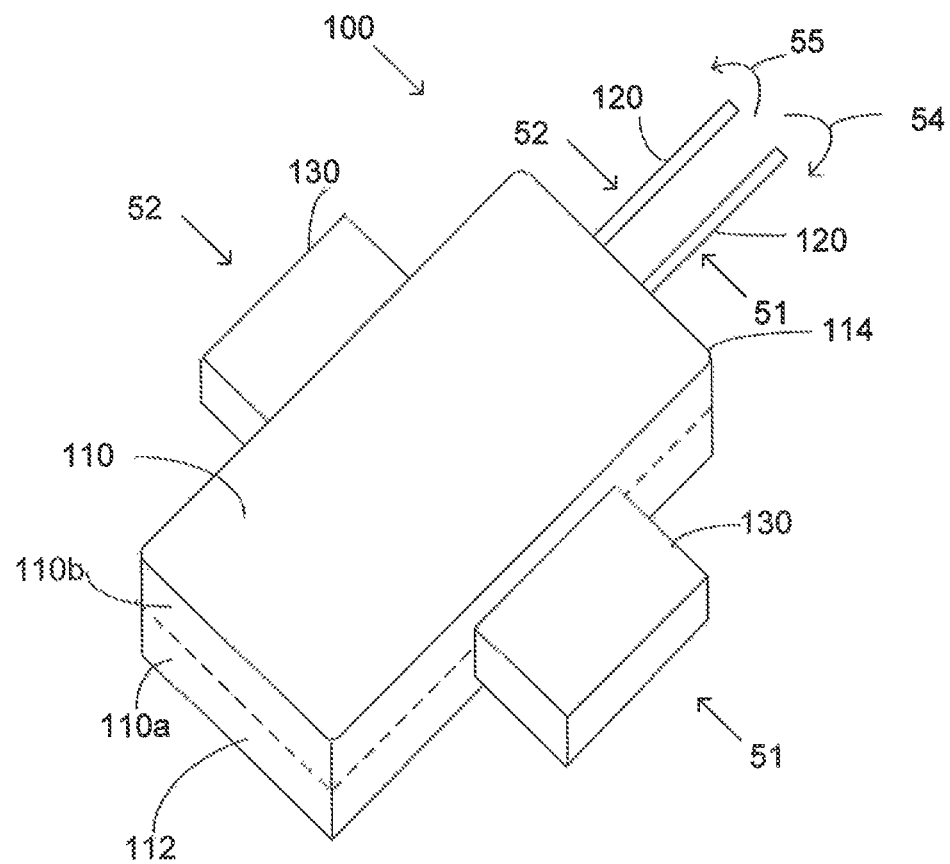
FIG. 1 shows a perspective view of a skin care apparatus in accordance with an example embodiment.

Reference will now be made in detail to several embodiments of the invention that are illustrated in the accompanying drawings. Wherever possible, same or similar reference numerals are used in the drawings, and the description, to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner. The words "connect," "couple" and similar terms do not necessarily denote direct and immediate connections, but may also include connections through intermediate elements or components.

FIG. 1 shows a perspective view of a skin care apparatus 100 in accordance with an example embodiment, The skin care apparatus (or simply "apparatus" or "device") 100 includes a housing 110 that encases, partially or completely, a plurality of components including actuators 130 and rotating members 120. At a high level, as the actuators 130 are pressed by a user in their respective directions shown by arrows 51, 52, rotating members 120 are forced towards each other in directions 51, 52 and, at least during a portion of their travel towards each other, rotate in directions that are counter to each other as indicated by circular arrows 54, 55. When the rotating members are placed against tissue, the resulting squeezing and rotating motion provides a desired application, of pressure on, or pinching of, the skin or other tissue.

In an embodiment, actuators 130 and rotating members 120, which are mechanically coupled to each other, are spring loaded and biased in directions opposite to respective arrows 51, 52 such that, when actuators 130 are in a non-depressed steady state, rotating members 120 are separated from each other by a steady state "fully separated" distance on the order of, e.g., 1-5 millimeters, and actuators 130 are disposed at their fully extended positions. When the actuators 130 are in their fully depressed state, rotating members 120 may be separated by a "nearest" distance of, e.g., 0.5-1 millimeter. The foregoing distance values are examples only, and those skilled in the art will appreciate that the embodiments of the present invention may be implemented with larger or smaller fully separated and nearest distances.

As will be shown in more detail in connection with FIG. 6B, distal ends of rotating members 120 may be provided with, e.g., an accessory such as a slip-on cover or attachment 615 that is configured to provide appropriate contact with skin or other tissue. The slip-on attachment 615 is, preferably, the only component that actually comes into contact with the skin or other tissue of a user. Slip-on attachments are preferably disposable and easily replaceable on the distal ends of rotating members 120. However, the distal ends of rotating members 120 may also, or instead, be configured with surface features and shapes that provide sufficient friction with tissue, thus obviating the need for the slip-on attachments.

Referring still to FIG. 1, housing 110 is shown as substantially rectangular, but other shapes for housing 110 are to be considered within the scope of the presently described invention. For example, housing 110 could have rounded edges and/or sides, could be oval or circular, or could be any other shape that might be beneficial for a user to more easily hold and operate the apparatus 100. As another example, housing 110 may be in the form of a pen or stylus.

Figure 2:
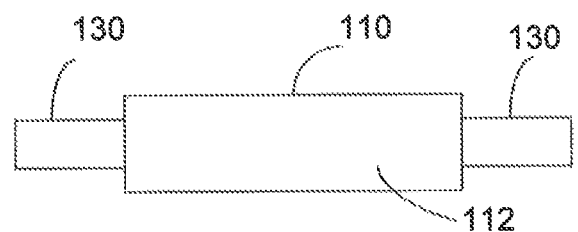
FIG. 2 shows a proximal end view of the skin care apparatus in accordance with an example embodiment.

FIG. 2 shows a proximal end view of the skin care apparatus in accordance with an example embodiment. As shown, proximal end 112 of housing 110 may be smooth, without any protruding components.

Figure 3:
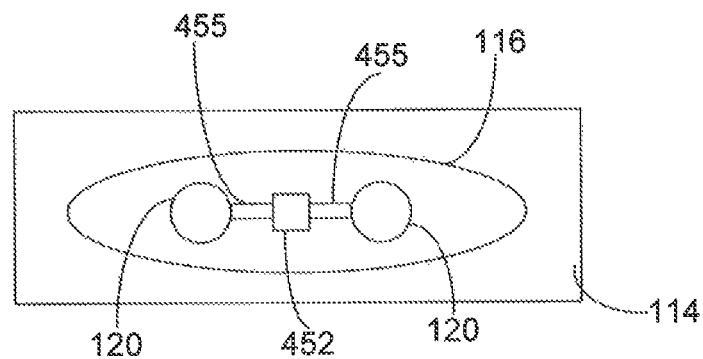
FIG. 3 shows a distal end view of the skin care apparatus in accordance with an example embodiment.

FIG. 3 shows a distal end view of the skin care apparatus 100 in accordance with an example embodiment. As shown, distal end 114 includes an opening 116 through which distal ends of rotating members 120 pass. Also shown through opening 116 is a stopper 452 and a spring 455, which are both discussed in detail in connection with FIG. 4.

Figure 4:
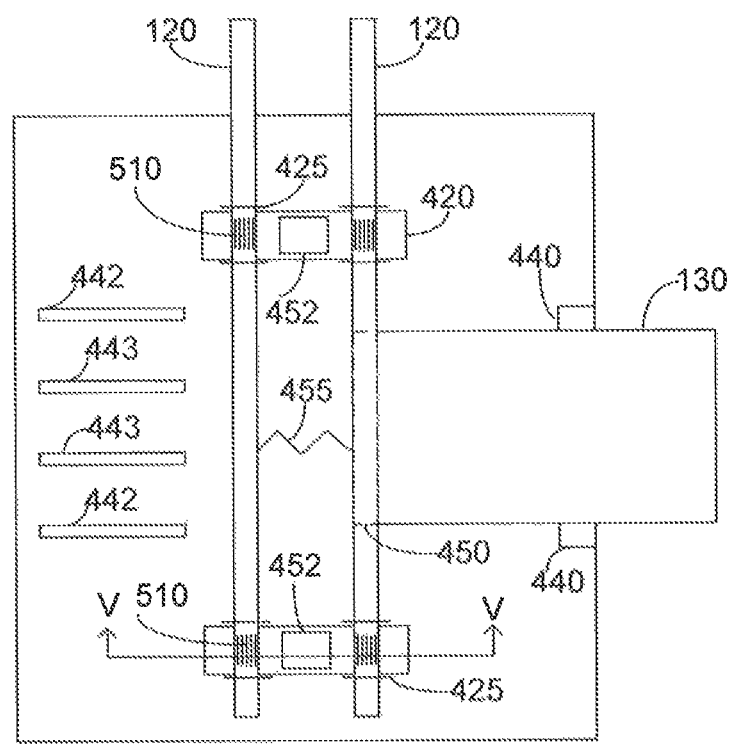
FIG. 4 shows a plan view of the skin care apparatus with a top portion of the housing removed in accordance with an example embodiment.

FIG. 4 shows a plan view of the skin care apparatus 100 with a top portion 110b of the housing 110 removed in accordance with an example embodiment. As mentioned above, embodiments of the present invention are configured to cause rotating members to both approach each other and rotate in directions counter to each other such that the distal ends of rotating members 120 can apply a desired outward pinching action to the skin or other tissue of a user.

FIG. 4 shows, e.g., a bottom portion 110a of housing 110 without a corresponding top cover or top portion 110b. When fully assembled, bottom portion 110a of the housing 110 and top portion 110b are brought together and attached to each other thereby sandwiching in place therebetween the several components shown in FIG. 4.

In the depicted embodiment, rotating members 120 are disposed in parallel to each other. In one implementation, they are disposed in at least one channel 420 that is, e.g., integrally formed with bottom portion 110a. FIG. 4 shows a bottom portion of the channel 420. A corresponding top portion of channel(s) 420 may be integrated with top portion 110b of housing 110. Rotating members 120, adjacent the channel(s) 420, may include one or more keepers 425 that abut channel 420. A keeper may be, e.g., an E-clip, or a protrusion integrally formed with rotating member 120. That is, keepers 425 may be, e.g., a feature having a diameter greater than the opening of the channel 420 such that rotating members 120 are captured within channels(s) 420 in both the Y-axis (along a longitudinal axis of the rotating members 120) and x-axis (along a longitudinal axis of the channel 420).

Actuators 130 (only one of which is shown in FIG. 4) are disposed in housing 110 such that they travel in a direction perpendicular to the longitudinal axis of the rotating members 120. Actuators 130 are in contact with rotating members 120 via a flat face, a curved face, a semi-circular curved face, or by entirely surrounding a rotating member 120. In the case where the rotating members 120 are entirely surrounded by actuator 130 (shown by broken line 450), keepers 425 may also, or instead, be disposed adjacent outside surfaces of actuator 130, or internal to the actuators 130 (not shown). To keep actuators 130 from falling out of housing 110, tabs 440 may be provided on, e.g., sides of the actuators 130 that come into contact with an inside surface of housing 110. Protrusions 442 may be provided as guides to keep actuators 130 in a proper track. In the same vein, a groove (or protrusion) (not shown) may be provided on a surface of actuator 130 that corresponds to a protrusion (or groove) 443 on an inside surface of housing 110 that mate and keep actuator 130 in a proper track. Those skilled in the art will appreciate that the foregoing description of approaches to mounting actuators 130 in housing 110 are only examples and other approaches may be implemented.

A spring 455 is provided to bias rotating members 120 and actuators 130 away from each other. When actuators 130 are pressed towards each other, e.g., by a user's fingers, rotating members 120 approach each other resulting in a squeezing action on the part of the rotating members 120.

Not only does the device 100 cause the rotating members 120 to approach each other in a squeezing action, but the device 100 also causes the rotating members to rotate in opposite directions with respect to one another to achieve (from the perspective of a user's skin) an outward pinching action.

FIG. 5 shows details of channel 420 that retains the rotating members 120 and that imparts the desired rotation in accordance with an example embodiment. As shown, channel 420 includes a bottom portion 505 and a top portion 506. Stopper 452, which may function as a safety mechanism, is disposed substantially equidistant from ends of channel 420, and is used to stop rotating members 120 from contacting each other when, using actuators 130, rotating members 120 are pushed towards each other as indicated by arrows 551, 552. In an embodiment, top portion 506 of channel 420 includes teeth 520 that engage with teeth 510 protruding from rotating members 120. The teeth 510 may be provided by a gear or gears fixed to the respective rotating members 120. Referring again to FIG. 4, teeth 510 of rotating members 120 may be disposed on only a portion of rotating members 120, namely in the vicinity of channel 420. In this way, actuators 130 may interact or engage with a smooth surface of rotating members 120. Also, in one possible implementation, only a portion of top portion 506 may include teeth 520 such that rotating members 120 may freewheel during at least part of the motion caused by actuators 130.

Referring again to FIG. 5, as rotating members 120 are pushed towards each other, teeth 510 engage with teeth 520 on the top portion 506 of recess 420 and cause rotating members 120 to rotate in directions counter to each other, as indicated by arrows 561, 562. As a result, not only do rotating members approach each other due to pressing on actuators 130, but rotating members 120 also rotate counter to each other and can thereby impart an outward pinching action to the skin or other tissue.

Although not to be construed as limiting, the teeth 510 and 520 may be arranged such that rotating members 120 rotate no more than, e.g., approximately ¼ turn. However, the amount of rotation can be configured by selecting an appropriate pitch for teeth 510, 520.

Also, in one possible implementation, stopper 452 may be adjustable such that, in their fully depressed state, rotating members 120 may be separated to different "nearest" distances to accommodate different size blemishes. In this regard, stopper 452 may be in the form of, e.g., a slidable or replaceable element (not shown) with stepped sizes to permit a user to select a desired "nearest" distance, including a "nearest" distance of zero.

In yet another embodiment, only one "rotating" member 120 may be provided, and is paired with another similar member that is fixed in position such that it does not rotate (or perhaps not move at all). A similar outward pinching action may still be possible with only a single rotating member 120 engaging the dermis in combination with a fixed member.

The several components described herein may be manufactured from various materials including stainless steel, plastic, or any other suitable material or combinations thereof.

In an embodiment, distal ends of rotating members 120 may or may not include an attachment or accessory. In one embodiment, distal ends of rotating members may be, e.g., bare metal or plastic with a surface feature that helps to promote gentle contact with the dermis with a view to limiting cutting or bruising of the skin or other tissue. For example, as shown in FIG. 6A (only one rotating member 120 is shown), the distal end of rotating member 120 may include a surface feature such as a plurality of dull protrusions, or lineal features 610. The surface feature could also be in the form of a diamond pattern, bumps, or may also be smooth.

In another embodiment, distal ends of rotating members 120 may be overmolded with, e.g., silicone or other suitable rubberized material that might impart a "stickiness" to an interface between the rotating members 120 and the dermis or other tissue.

In still another embodiment, and as shown in FIG. 6B, an accessory or attachment in the form of, e.g., a (slip on) cover 615 may be provided for the tip or distal end of rotating member 120. The cover 615 may be made of a rubberized (e.g., silicone) material impregnated and/or wrapped with gauze or cotton-like material to impart a stickiness or "tooth" to an interface between the distal end of rotating member 120 and the dermis or other tissue, and also to absorb any secretions resulting from the outward pinching action provided by the apparatus 100. Cover 615 need not have any such absorbing feature, however. Although cover 615 is shown as having a substantially cylindrical shape, cover 615 may take on any shape such as a cone, or conical section, a square or rectangle, a semi-circular shape, etc. Likewise, the distal ends of rotating members 120 can also be in the form of other shapes.

To ensure that slip on cover 615 rotates along with rotating member 120, a key 620 in the form of, e.g., a protrusion, may be provided on the distal end of rotating member 120, and the cover 615 may have a corresponding cut out (not shown) on an inside surface thereof that engages with the key 620 of rotating member 120. In another embodiment, the cross-section of the distal end of the rotating member 120 may have a predetermined shape other than circular, e.g., triangular, square, pentagonal, octagonal, and the cover 615 may have an internal shape that matches the predetermined cross-sectional shape. In one implementation, cover 615 is friction fit with the distal end of rotating member 120 (or fixed member), and can thus be easily placed on and removed by hand, without any special tools.

In an embodiment, cover 615 may be disposable and sold separately from the apparatus 100. In this way, different types of slip on covers may be obtained and used with the apparatus at a user's discretion.

In one implementation, rotating members 120 are rigid elements that do not bend. However, in another implementation, rotating members may be relatively flexible, particularly towards the distal ends thereof such that a user can more comfortably position the housing 110 and rotating members 120 near the intended tissue contact area.

Further, the disclosed embodiments focused on a geared mechanism to impart the rotating motion to the rotating members. However, those skilled in the art will appreciate that other mechanisms may be implemented. For example, a mechanism that translates linear motion (of the actuators) into rotational motion using, e.g., a crank (not shown in the figures) could be implemented. Further, the rotational members may be turned by electric motors directly, or, e.g., through gears or a crank mechanism. A pneumatic or hydraulic mechanism may also be implemented to achieve the rotating action of at least one of the rotating members 120.

Figure 7A:
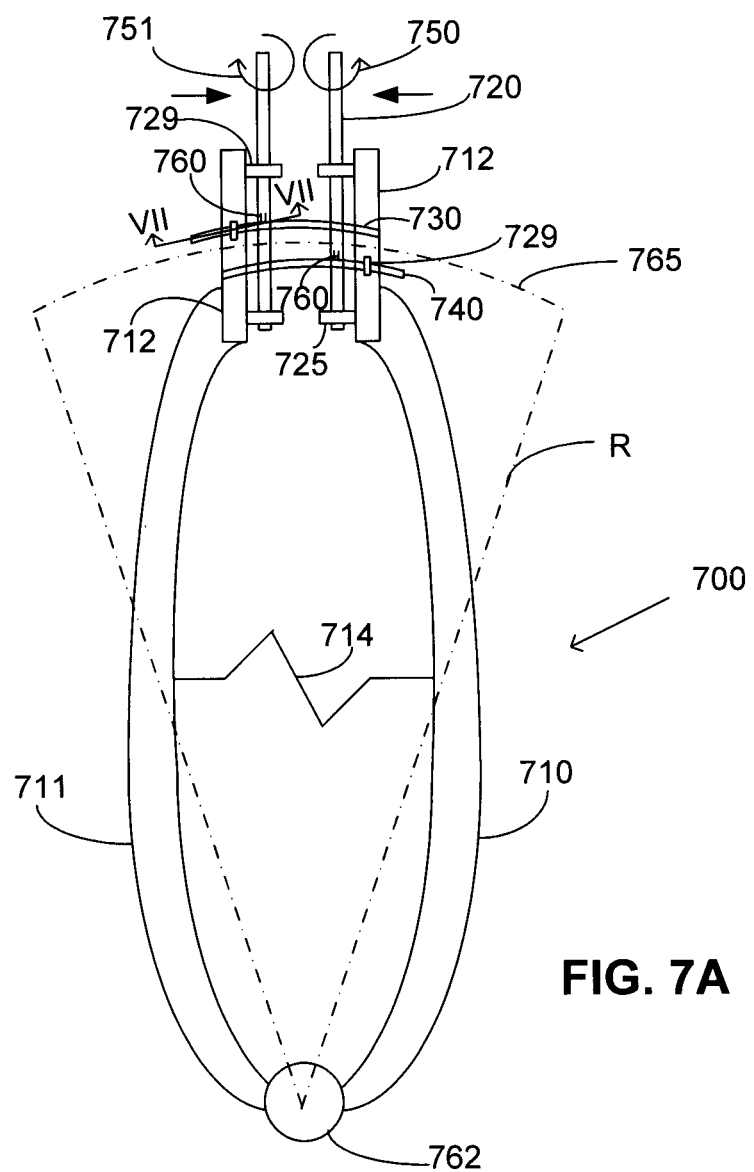
FIG. 7A depicts a plan view of another embodiment of the present invention in accordance with an example embodiment.

FIG. 7A depicts a plan view of another embodiment of the present invention. The embodiment of FIG. 7A is configured substantially in the form of a tweezer 700 having two arms 710, 711 fused together at one end, or pivoted with respect to each other via, e.g., a hinge 762. Rotating members 720 are mounted to (or within) extensions 712 of arms 710, 711 via bearings 725. Rotating members 720 may be secured in a longitudinal axis direction by E-clips (not shown) or other means, such as those described in connection with the prior embodiment.

Also provided are rotation imparting members 730 and 740. In an embodiment, rotation imparting member 730 is fixed to extension 712 of arm 710, and rotation imparting member 740 is fixed to extension 712 of arm 711. Rotation imparting members 730, 740 may be toothed racks that engage with, e.g., respective gears 760 on rotating members 720. As such, when tweezer arms 710, 711 are squeezed together, rotation imparting members 730, 740 are forced towards each other and cause rotating members 720 to rotate in opposite directions with respect to each other as indicated by arrows 750, 751. Arms 710, 711 may be biased away from each other via a spring 714. Further, rotation imparting members 730, 740 may, as shown, be curved with a curvature that matches an arc of rotation 765 defined by a radius R from a pivot point of the arms 710, 711 (e.g., hinge 762) and the location of the respective gear(s) 760.

Figure 7B:
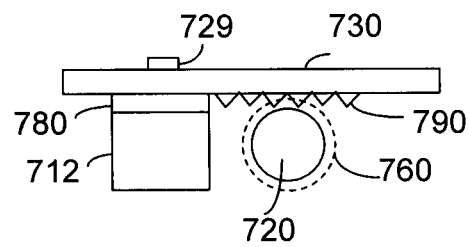
FIG. 7B is a cross-sectional view taken at VII-VII shown in FIG. 7A, and shows a rotation imparting member engaging with a gear, which is affixed to a rotating member, in accordance with an example embodiment.

FIG. 7B is a cross-sectional view taken at VII-VII shown in FIG. 7A, and shows one extension 712 and teeth 790 of rotation imparting member 730 engaging with gear 760, which is affixed to rotating member 720. A guide 729, such as a slot that is fixed to extension 712 and through which rotation imparting member 730 may slide, ensures that rotation imparting member 730 stays strongly engaged with gear 760. A groove or recess 780 may be provided in extension 712 to enable teeth 790 of the rack gear of rotation imparting member 730 to transit across extension 712. Although a rack gear and simple wheel gear 760 are shown, rotation imparting members 730, 740 and gears 760 may be bevel gears or any other type of system that translates linear motion into circular motion.

Thus, in the embodiment of FIGS. 7A and 7B, not only do rotating members 720 approach each other when the tweezer 700 is squeezed, but rotating members 720 also rotate counter to each other to thereby impart an outward pinching action when the rotating members 720 are pressed against tissue such as the dermis. The tips or distal ends of rotating members 720 may also be provided with covers or accessories as described in connection with the previous embodiment. Further, in the embodiment of FIGS. 7A and 7B only one rotating member may be configured to rotate using only one rotation imparting member, while the other "rotating member" is fixed.

Finally, although rotation members 720 are shown exposed outside of extensions 712, in one possible implementation, rotation members 720 can, alternatively, be enclosed within extensions 712. Also, as described in the prior embodiment, rotation imparting members 730, 740 may not include teeth 790 along an entire length thereof thereby allowing rotating members 720 to freewheel during at least part of the approaching motion of arms 710, 711.

Figure 8:
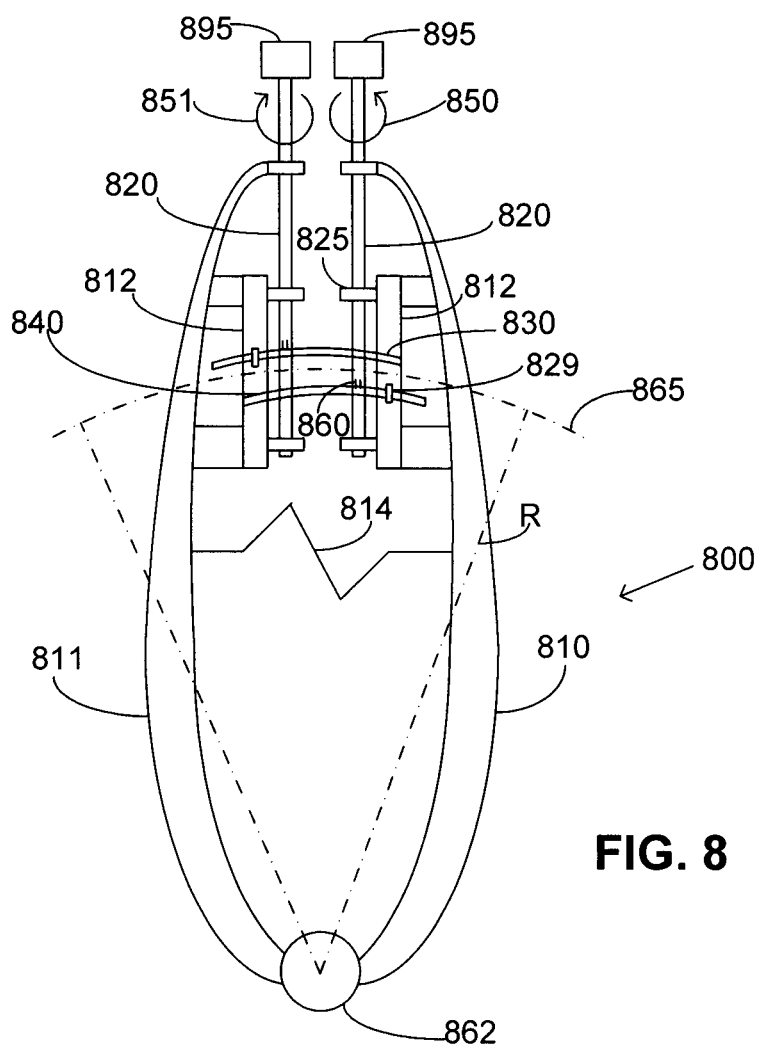
FIG. 8 depicts a plan view of yet another embodiment of the present invention.

FIG. 8 depicts a plan view of yet another embodiment of the present invention. The embodiment of FIG. 8 is configured substantially in the form of a tweezer 800 having two arms 810, 811 fused together at one end, or pivoted with respect to each other via, e.g., a hinge 862. Rotating members 820 are mounted to (or within) extensions 812 of arms 810, 811 via bearings 825. Rotating members 820 may be secured in a longitudinal axis direction by E-clips (not shown) or other means, such as those described in connection with the prior embodiment.

Also provided are rotation imparting members 830 and 840. In an embodiment, rotation imparting member 830 is fixed to extension 812 of arm 810, and rotation imparting member 840 is fixed to extension 812 of arm 811. Rotation imparting members 830, 840 may be toothed racks that engage with, e.g., respective gears 860 on rotating members 820. As such, when tweezer arms 810, 811 are squeezed together, rotation imparting members 830, 840 are forced towards each other and cause rotating members 820 to rotate in opposite directions with respect to each other as indicated by arrows 850, 851. Arms 810, 811 may be biased away from each other via a spring 814. Further, rotation imparting members 830, 840 may, as shown, be curved with a curvature that matches an arc of rotation 865 defined by a radius R from a pivot point of the arms 810, 811 (e.g., hinge 862) and the location of the respective gear(s) 860. Guides 829 may be provided on extensions 812, as in the embodiment described in connection with FIGS. 7A and 7B.

The main difference between the embodiment of FIG. 8 and that shown in FIG. 7A is that the rotation imparting members 830, 840 are disposed within a region between arms 810, 811, as opposed to a region beyond arms 710, 711, as shown in FIG. 7A.

Finally, as further shown in FIG. 8, the distal ends 895 of rotating members 820 may be configured to have diameters or shapes sufficient to come into contact with each other prior to, e.g., any of the bearings 825 contacting each other as arms of the tweezer 800 (or 700 of FIG. 7A) are squeezed.

Having described preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

What is claimed is:

1. A skin care device comprising:
a first arm having a first rotating member including a first gear coupled thereto and a first toothed rack fixed thereto; and
a second arm pivotally coupled to the first arm, about a pivot axis, at proximal ends of the first arm and the second arm, the second arm having a second rotating member including a second gear coupled thereto and a second toothed rack fixed thereto,
wherein the skin care device is configured such that when the first arm and the second arm are brought towards each other, the first toothed rack engages with the second gear to cause the second rotating member to rotate in a first direction, and the second toothed rack engages with the first gear to cause the first rotating member to rotate in a second direction, opposite the first direction,
wherein the first rotating member has a first longitudinal axis about which the first rotating member rotates, and
wherein the first longitudinal axis is perpendicular to the pivot axis.

2. The skin care device of claim 1, wherein at least one of the first toothed rack or the second toothed rack is curved.

3. The skin care device of claim 2, wherein a curvature of the first toothed rack substantially matches an arc of rotation defined by a radius that extends from a pivot point of the first arm and the second arm and a location of the second gear.

4. The skin care device of claim 2, wherein a curvature of the second toothed rack substantially matches an arc of rotation defined by a radius that extends from a pivot point of the first arm and the second arm and a location of the first gear.

5. The skin care device of claim 1, wherein the first arm further comprises a guide through which the second toothed rack slides.

6. The skin care device of claim 1, wherein the second arm further comprises a guide through which the first toothed rack slides.

7. The skin care device of claim 1, wherein a distal end of the first rotating member comprises a surface feature.

8. The skin care device of claim 1, wherein a distal end of the first rotating member comprises a key.

9. The skin care device of claim 8, wherein the key is configured to engage with a slip-on accessory that fits on the distal end of the first rotating member.

10. The skin care device of claim 1, further comprising an accessory that slips over a distal end of the first rotating member.

11. The skin care device of claim 10, wherein the accessory comprises a slip-on cover.

12. The skin care device of claim 11, wherein the slip-on cover comprises an absorbent material.

13. The skin care device of claim 11, wherein the slip-on cover comprises silicone.

14. The skin care device of claim 1, wherein at least a portion of one of the first arm or the second arm is straight.

15. The skin care device of claim 1, wherein at least a portion of one of the first arm or the second arm is curved.

16. The skin care device of claim 1, further comprising a spring that biases the first arm away from the second arm.

17. The skin care device of claim 1, wherein the first rotating member and the second rotating member are made from stainless steel.

18. The skin care device of claim 1, wherein the first rotating member and the second rotating member are made from plastic.

19. A skin care device comprising:
a first arm;
a second arm connected at one end thereof to one end of the first arm at a pivot point having a pivot axis about which the first arm pivots with respect to the second arm;

the first arm including a first rotating member connected thereto by at least one first bearing, the first rotating member including a first gear and a first longitudinal axis;

the second arm including a second rotating member connected thereto by at least one second bearing, the second rotating member including a second gear and a second longitudinal axis;

the first arm further including a first toothed rack; and the second arm further including a second toothed rack, wherein the skin care device is configured such that when the first arm and the second arm are pivoted towards each other, the first toothed rack engages with the second gear to cause the second rotating member to rotate in a first direction around the second longitudinal axis, and the second toothed rack engages with the first gear to cause the first rotating member to rotate in a second direction around the first longitudinal axis, opposite the first direction, wherein the first longitudinal axis and the second longitudinal axis are each perpendicular to the pivot axis.

20. A skin care device comprising:

a first arm including a first toothed rack and a first rotating member, the first rotating member having a first longitudinal axis and comprising a first gear; and a second arm including a second toothed rack and a second rotating member, the second rotating member having a second longitudinal axis and comprising a second gear, wherein the first arm and the second arm are coupled at a coupling location at proximal ends thereof, wherein the skin care device is configured such that when the first arm and the second arm are brought towards each other, the first toothed rack engages with the second gear to cause the second rotating member to rotate in a first direction about the second longitudinal axis, and the second toothed rack engages with the first gear to cause the first rotating member to rotate in a second direction about the first longitudinal axis, opposite the first direction, and wherein the first rotating member and the second rotating member extend along the first longitudinal axis and the second longitudinal axis, respectively, from first positions, located between the coupling location and distal ends of the first arm and the second arm, to second positions, located beyond the distal ends of the first arm and the second arm.

* * * * *